United States Patent [19]
Hosaka et al.

[11] Patent Number: 5,649,543
[45] Date of Patent: Jul. 22, 1997

[54] PULSE-WAVE PROPAGATION TIME BASIS BLOOD PRESSURE MONITOR

[75] Inventors: Hidehiro Hosaka; Hiroshi Sakata; Yoshihiro Sugo; Takeshi Sohma; Hiromitsu Kasuya, all of Tokyo, Japan

[73] Assignee: Nihon Kohden Corporation, Tokyo, Japan

[21] Appl. No.: 466,746

[22] Filed: Jun. 6, 1995

[30] Foreign Application Priority Data

Jun. 6, 1994 [JP] Japan .................................. 6-123653

[51] Int. Cl.$^6$ .................................................. A61B 5/00
[52] U.S. Cl. ......................... 128/681; 128/682; 128/687
[58] Field of Search ..................... 128/687, 672, 128/677, 680–683

[56] References Cited

U.S. PATENT DOCUMENTS

| | | | |
|---|---|---|---|
| 4,807,638 | 2/1989 | Sramek | 128/672 |
| 4,907,596 | 3/1990 | Schmid et al. | 128/672 |
| 5,237,997 | 8/1993 | Greubel et al. | 128/687 |
| 5,241,964 | 9/1993 | McQuilkin | 128/672 |
| 5,309,916 | 5/1994 | Hatschek | 128/672 |

*Primary Examiner*—Robert L. Nasser
*Attorney, Agent, or Firm*—Sughrue, Mion, Zinn, Macpeak & Seas

[57] ABSTRACT

A pulse-wave propagation time basis blood pressure monitor includes a memory for storing an equation describing the relationship between the pulse wave propagation time and the parameter $\alpha$, input means for entering the blood pressure value for calibration, a time-interval detect reference point detecting means for detecting a reference point for detecting the time interval of a pulse wave in the aorta of a subject; pulse wave detecting means for detecting a pulse wave which appears in the peripheral blood vessel after it appears in the aorta; pulse-wave propagation time measuring section for measuring a pulse wave propagation time from the output signals of the time-interval detect reference point detecting means and the pulse wave detecting means, first computing means for determining the parameter $\alpha$ proper to the subject on the basis of the general equation stored in the memory by using the pulse wave propagation time for calibration gathered from the subject, second computing means for determining the parameter $\beta$ to be added in computing a blood pressure value by using the pulse wave propagation time, by using the blood pressure value inputted for calibration, the pulse wave propagation time measured for calibration, and the parameter $\alpha$ determined by the first computing means, third computing means for computing a blood pressure value by using the measured pulse wave propagation time, and the parameters $\alpha$ and $\beta$, and measured data output means for outputting data of the computed blood pressure value.

7 Claims, 7 Drawing Sheets

| PULSE WAVE PROPAGATION TIME $T_0$ [msec] | PARAMETER $\alpha$ |
|---|---|
| ~140 | -0.7 |
| 139~125 | -1.0 |
| 124~110 | -1.5 |
| 109~95 | -2.0 |
| 94~ | -3.0 |

| PULSE PRESSURE $P_a$ [mmHg] | PARAMETER $\alpha$ |
|---|---|
| ~45 | -0.7 |
| 46~55 | -1.0 |
| 56~65 | -1.5 |
| 66~75 | -2.0 |
| 76~ | -3.0 |

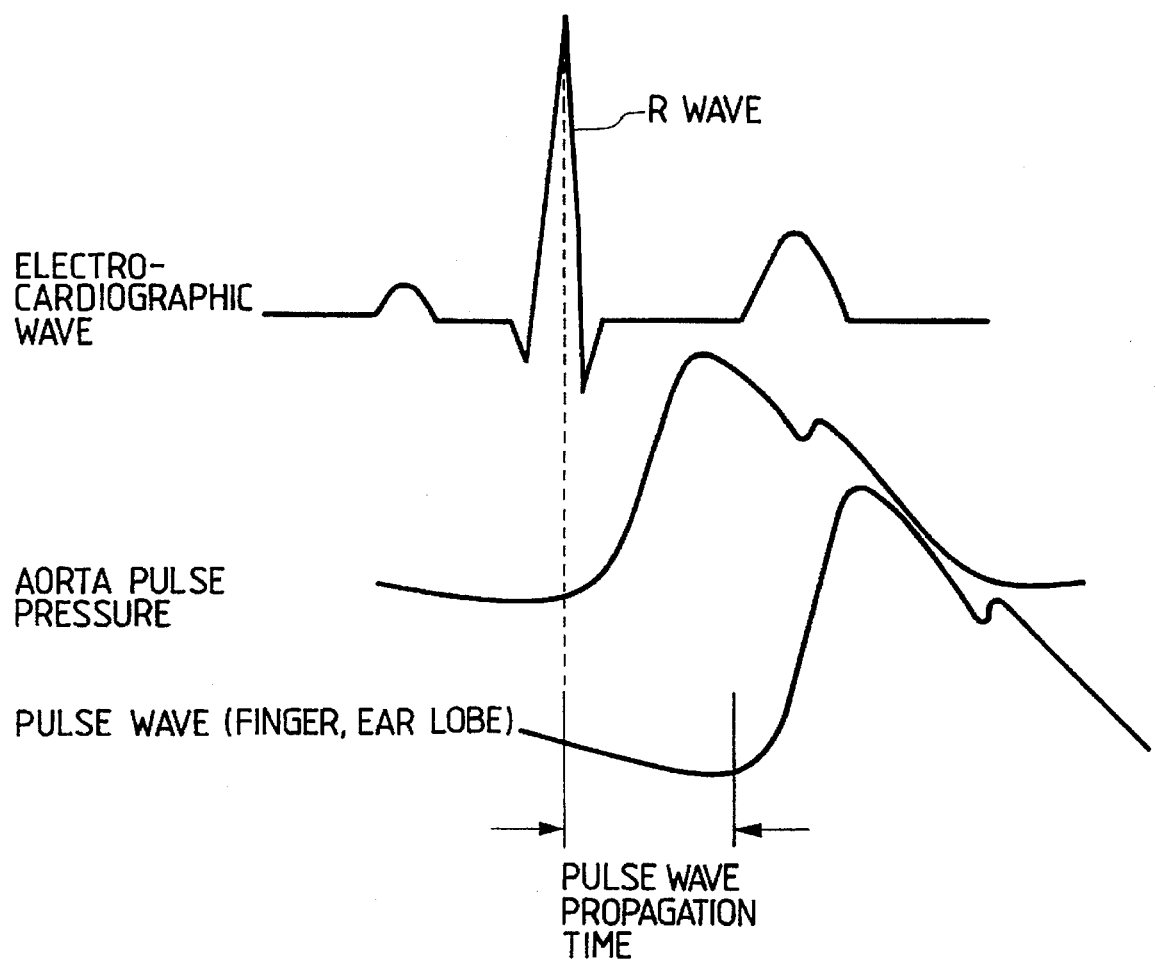

PULSE-WAVE PROPAGATION TIME BASIS BLOOD PRESSURE MONITOR

BACKGROUND OF THE INVENTION

1. Field of the Invention

The present invention relates to a pulse-wave propagation time basis blood pressure monitor suitable for a stress test blood pressure monitor, a blood pressure monitor of the Holter type, and a blood pressure monitor used in a care room, which are used in a field where a non-restrictive, successive and noninvasive blood pressure measurement is required for a subject. More particularly, the present invention relates to a blood pressure monitor for measuring parameter values used when blood pressure is measured by using the pulse wave propagation time without greatly varying blood pressure in a stress test, for example.

2. Related art

A blood pressure monitor using a cuff has been known as a noninvasive blood pressure monitor which is capable of measuring a blood pressure in a successive and noninvasive fashion.

In this type of blood pressure monitor, the cuff must be wound on the upper part of an arm. Accordingly, the arm is restricted by the cuff wound thereon, the weight of the cuff is for the subject to bear, and the subject's sleep will be disturbed by squeezing the arm by the cuff or noise generated when the cuff is handled.

To continuously monitor blood pressure values of a subject, when the measurement interval is 5 minutes or longer, an abrupt change of a blood pressure by a shock is possibly passed unmarked.

One of the possible ways to solve this problem is to reduce the measuring interval to about one minute. In this case, the tightening of the arm by the cuff is frequently repeated, to thereby increase a load to the subject and to the blood vessels in the portion wound by the cuff. In the extreme case, inner hemorrhage may be caused in the subject.

For the noninvasive blood pressure monitor which succeeds in solving the problems of the above-mentioned blood pressure monitor, there is known a blood pressure monitor for measuring a blood pressure by making use of a pulse wave propagation velocity (pulse wave propagation time for a fixed time).

The principle of measuring a blood pressure on the basis of a pulse wave propagation velocity will be described.

The pulse wave propagation time will first be described. As shown in FIG. 9, a specific point of a pulse wave appears in the peripheral blood vessel of the finger or the ear later than in the aorta. This delay time is a pulse wave propagation time.

A pulse wave propagation velocity corresponding to a pulse wave propagation time for a fixed distance is expressed as the function of a volumetric elasticity of the vessel. When a blood pressure rises, the volumetric elasticity of the vessel increases, the wall of the vessel becomes hard, and the pulse wave propagation velocity increases.

As a consequence, a variation of the blood pressure can be obtained from the pulse wave propagation velocity.

The blood pressure monitor based on the pulse wave propagation time must be calibrated by the values of the blood pressure measured by a blood pressure measuring method which uses the cuff or other suitable means.

For the calibration, the blood pressure and the pulse wave propagation time are measured at rest and at excercise stress, for example.

Assuming that the blood pressure and the pulse wave propagation times at rest are P1 and T1, the blood pressure and the pulse wave propagation times at excercise stress are P2 and T2, and constants (parameters) proper to subjects are $\alpha$ and $\beta$, then the blood pressure P1 and P2 are expressed by $$P1 = \alpha T1 + \beta$$

$$P2 = \alpha T2 + \beta$$

As seen from these equations, if P1, T1, P2, and T2 are determined by measurement, the parameters $\alpha$ and $\beta$ can be calculated. If these parameters are determined, a blood pressure of a subject can be obtained by merely measuring the pulse wave propagation time.

Thus, in the blood pressure monitor using the pulse wave propagation time, the calibration for determining the parameters $\alpha$ and $\beta$ is inevitably required. For the calibration, a stress test must be carried out on the subject. The test puts a strain on the subject, and much time is taken for the calibration.

Additionally, a stress test device or a blood pressure monitor exclusively used for the stress test must used, thereby increasing the device cost.

SUMMARY OF THE INVENTION

Accordingly, an object of the present invention is to provide a pulse-wave propagation time basis blood pressure monitor which can measure a blood pressure on the basis of the pulse wave propagation time without increasing the time for the calibration to determine the parameters $\alpha$ and $\beta$ and putting a strain to the subject.

According to an aspect of the present invenion, there is provided a pulse-wave propagation time basis blood pressure monitor comprising:

a memory for storing a general equation describing the relationship between the pulse wave propagation time and the parameter $\alpha$, in computing blood pressure values from the pulse wave propagation time, the pulse wave propagation time being derived from data gathered from a number of subjects in order to determine the parameter $\alpha$ that is proper to each subject and to be multiplied by the pulse wave propagation time;

input means for inputting blood pressure values of subjects that are for calibration;

time-interval detect reference point detecting means for detecting a reference point for detecting the time interval of a pulse wave in the aorta of a subject;

pulse wave detecting means for detecting a pulse wave which appears in the peripheral blood vessel after it appears in the aorta;

pulse-wave propagation time measuring means for measuring a pulse wave propagation time from the output signals of the time-interval detect reference point detecting means and the pulse wave detecting means;

first computing means for determining the parameter $\alpha$ proper to the subject on the basis of the general equation stored in the memory by using the pulse wave propagation time for calibration gathered from the subject;

second computing means for determining the parameter $\beta$ to be added in computing a blood pressure value by using the pulse wave propagation time, by using the blood pressure value inputted for calibration, the pulse wave propagation time measured for calibration, and the parameter $\alpha$ determined by the first computing means;

third computing means for computing a blood pressure value by using the measured pulse wave propagation time, and the parameters $\alpha$ and $\beta$; and measured data output means for outputting data of the computed blood pressure value.

The first technical idea may also be realized by a pulse-wave propagation time basis blood pressure monitor comprising:

a memory for storing a table describing the relationship between the pulse wave propagation time and the parameter $\alpha$, in computing blood pressure values from the pulse wave propagation time, the pulse wave propagation time being derived from data gathered from a number of subjects in order to determine the parameter $\alpha$ that is proper to each subject and to be multiplied by the pulse wave propagation time;

input means for inputting blood pressure values of subjects that are for calibration;

time-interval detect reference point detecting means for detecting a reference point for detecting the time interval of a pulse wave in the aorta of a subject;

pulse wave detecting means for detecting a pulse wave which appears in the peripheral blood vessel after it appears in the aorta;

pulse-wave propagation time measuring means for measuring a pulse wave propagation time from the output signals of the time-interval detect reference point detecting means and the pulse wave detecting means;

first computing means for determining the parameter $\alpha$ on the basis of the contents of the table stored in the memory by using the pulse wave propagation time for calibration gathered from the subject;

second computing means for determining the parameter $\beta$ to be added in computing a blood pressure value by using the pulse wave propagation time, by using the blood pressure value inputted for calibration, the pulse wave propagation time measured for calibration, and the parameter $\alpha$ determined by the first computing means;

third computing means for computing a blood pressure value by using the measured pulse wave propagation time, and the parameters $\alpha$ and $\beta$; and measured data output means for outputting data of the computed blood pressure value.

According to another aspect of the present invention, there is provided a pulse-wave propagation time basis blood pressure monitor comprising:

a memory for storing a general equation describing the relationship between the pulse pressure and the parameter $\alpha$, in computing blood pressure values from the pulse wave propagation time, the pulse wave propagation time being derived from data gathered from a number of subjects in order to determine the parameter $\alpha$ that is proper to each subject and to be multiplied by the pulse wave propagation time;

input means for inputting blood pressure values of subjects that are for calibration;

pulse pressure computing means for computing a pulse pressure for calibration using a blood pressure valve received from the input means;

time-interval detect reference point detecting means for detecting a reference point for detecting the time interval of a pulse wave in the aorta of a subject;

pulse wave detecting means for detecting a pulse wave which appears in the peripheral blood vessel after it appears in the aorta;

pulse-wave propagation time measuring means for measuring a pulse wave propagation time from the output signals of the time-interval detect reference point detecting means and the pulse wave detecting means;

first computing means for determining the parameter $\alpha$ proper to the subject on the basis of the general equation stored in the memory by using the pulse pressure for calibration gathered from the subject;

second computing means for determining the parameter $\beta$ to be added in computing a blood pressure value by using the pulse wave propagation time, by using the blood pressure value inputted for calibration, the pulse wave propagation time measured for calibration, and the parameter $\alpha$ determined by the first computing means;

third computing means for computing a blood pressure value by using the measured pulse wave propagation time, and the parameters $\alpha$ and $\beta$; and measured data output means for outputting data of the computed blood pressure value.

The second technical idea may also be realized by a pulse-wave propagation time basis blood pressure monitor comprising:

a memory for storing a table describing the relationship between the pulse pressure and the parameter $\alpha$, in computing blood pressure values from the pulse wave propagation time, the pulse wave propagation time being derived from data gathered from a number of subjects in order to determine the parameter $\alpha$ that is proper to each subject and to be multiplied by the pulse wave propagation time;

input means for inputting blood pressure values of subjects that are for calibration;

pulse pressure computing means for computing a pulse pressure for calibration using a blood pressure value received from the input means;

time-interval detect reference point detecting means for detecting a reference point for detecting the time interval of a pulse wave in the aorta of a subject;

pulse wave detecting means for detecting a pulse wave which appears in the peripheral blood vessel after it appears in the aorta;

pulse-wave propagation time measuring means for measuring a pulse wave propagation time from the output signals of the time-interval detect reference point detecting means and the pulse wave detecting means;

first computing means for determining the parameter $\alpha$ proper to the subject on the basis of the table stored in the memory by using the pulse pressure for calibration gathered from the subject;

second computing means for determining the parameter $\beta$ to be added in computing a blood pressure value by using the pulse wave propagation time, by using the blood pressure value inputted for calibration, the pulse wave propagation time measured for calibration, and the parameter $\alpha$ determined by the first computing means;

third computing means for computing a blood pressure value by using the measured pulse wave propagation time, and the parameters $\alpha$ and $\beta$; and measured data output means for outputting data of the computed blood pressure value.

According to another aspect of the present invention, there is provided a pulse-wave propagation time basis blood pressure monitor comprising:

first input means for inputting at least a patient's height value as patient information;

second input means for inputting a blood pressure value for calibration;

time-interval detect reference point detecting means for detecting a reference point for detecting the time interval of a pulse wave in the aorta of a subject;

pulse wave detecting means for detecting a pulse wave which appears in the peripheral blood vessel after it appears in the aorta;

pulse-wave propagation time measuring means for measuring a pulse wave propagation time from the output signals of the time-interval detect reference point detecting means and the pulse wave detecting means;

first computing means for computing a change ΔT of the pulse wave propagation time at the time of postural change by using the pulse wave propagation time for calibration measured at the supine position and the pulse wave propagation time for calibration measured at the sitting or standing position;

second computing means for computing a change ΔP of a hydrostatic pressure between the heart and a pulse wave measuring position at the time of postural change, by using a patient's height as patient information;

third computing means for determining the parameter α to be multiplied by the pulse wave propagation time in computing blood pressure values from the pulse wave propagation time, by using the change ΔT of the pulse wave propagation time and the change ΔP of the hydrostatic pressure;

fourth computing means for determining the parameter β to be multiplied by the pulse wave propagation time in computing blood pressure values from the pulse wave propagation time, by using the blood pressure value inputted for calibration, the pulse wave propagation time inputted for calibration, and the parameter α determined by the third computing means;

fifth computing means for computing a blood pressure value by using the measured pulse wave propagation time, and the parameters α and β; and measured data output means for outputting data of the computed blood pressure value.

As described above, the pulse-wave propagation time basis blood pressure monitor can determine the parameter α by using the pulse wave propagation time measured for calibration while using the general equation stored in the memory or referring to the table also stored in the memory.

After the parameter α is determined, the parameter β can be determined by using the parameter α, the blood pressure value inputted for calibration, and the pulse wave propagation time measured for calibration.

In the process of calibration for determining the parameters α and β, all one has to do is to measure a blood pressure one time.

After the parameters α and β, a blood pressure of a patient can be measured by using these parameters α and β and the pulse wave propagation time subsequently measured.

The pulse-wave propagation time basis blood pressure monitor can determine the parameter α by using the blood pressure value input for calibration while using the general equation stored in the memory or referring to the table also stored in the memory.

After the parameter α is determined the parameter β can be determined by using the parameter α, the blood pressure value input for calibration, and the pulse wave propagation time measured for calibration.

In the process, of calibration for determining the parameters α and β, all one has to do is to measure a blood pressure one time.

The pulse-wave propagation time basis blood pressure monitor can compute a change ΔP of a hydrostatic pressure between the heart and a pulse wave measuring position at the time of postural change, by using a patient's height as patient information, and determines the parameter α by using the change ΔP of the hydrostatic pressure and the change ΔT of the pulse wave propagation time at the time of postural change.

After the parameter α is determined, the parameter β can be determined by using the parameter α, the blood pressure value inputted for calibration, and the pulse wave propagation time measured for calibration.

Thus, also in this invention, in the process of calibration for determining the parameters α and β, all one has to do is to measure a blood pressure one time.

BRIEF DESCRIPTION OF THE DRAWINGS

FIG. 2 is a table showing the relationship between the pulse wave propagation time and the parameter α, the table being stored into a ROM of the blood pressure monitor of FIG. 1;

FIG. 3 is another table showing the relationship between the pulse wave propagation time and the parameter α, the table being stored into a ROM of the blood pressure monitor.

FIG. 9 is a diagram showing waveforms for explaining the pulse wave propagation time.

BRIEF DESCRIPTION OF THE PREFERRED EMBODIMENTS

The preferred embodiments of the present invention will be described with reference to the accompanying drawings.

First Embodiment

The basic idea of a first embodiment of the present invention will first be described.

There is a correlation between the volumetric elasticity of the vessel and the parameter α. Further, there is a correlation between the volumetric elasticity of the vessel and the propagation time of the pulse wave in the blood pressure at the same blood pressure value.

Hence, there is a correlation between the parameter α and the pulse wave propagation time.

The present invention is based on this knowledge.

The relationship between the pulse wave propagation time and the parameter α at rest was measured. The measurement was carried out on a total of 46 subjects including men of health and patients of 22 to 80 years old. The results of the measurement are as shown in FIG. 7.

Figure 7:
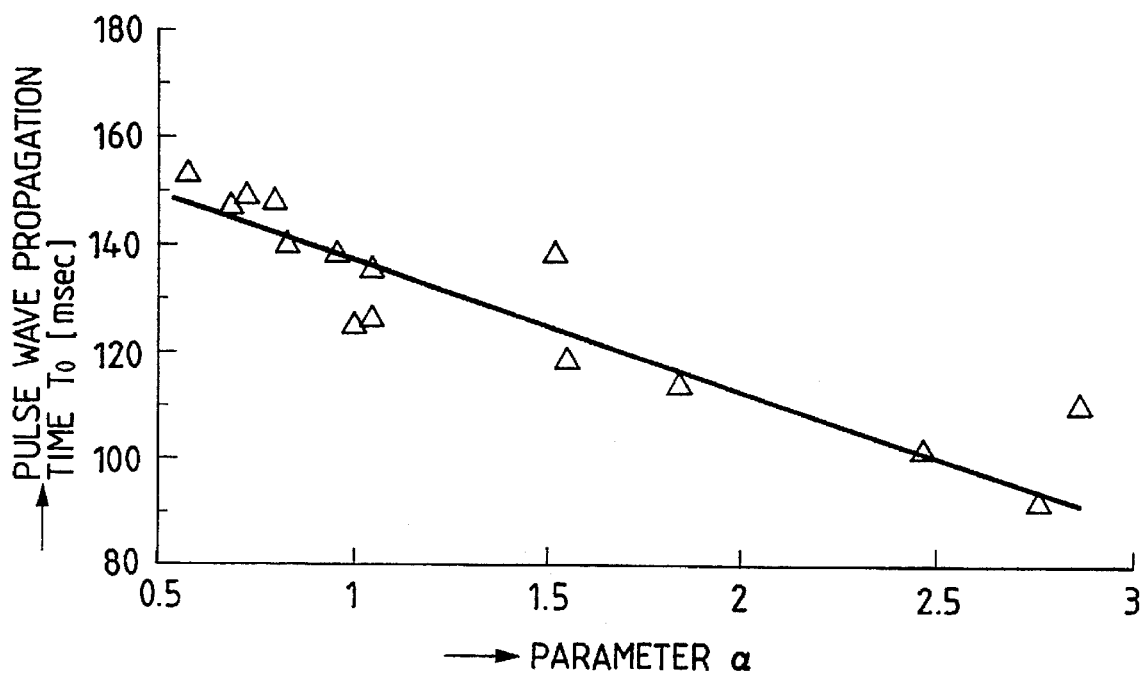
FIG. 7 is a graph showing the relationship between the pulse wave propagation time and the parameter α, both being actually measured.

As seen from the graph of FIG. 7, the pulse wave propagation time To and the parameter $\alpha$ can be expressed by the following equations $$To=-25\alpha+162$$

$$\alpha=-(To-162)/25 \quad (1)$$

The relationship between pulse wave propagation time To and the parameter $\alpha$ may approximately be described by a table TB1 as shown in FIG. 2 on the basis of the equation (1). In the table TB1, the pulse wave propagation time To is segmented every 15 msec.

As shown, in the table TB1, $\alpha$ (parameter) is –0.7 for 140 msec or longer of To (pulse wave propagation time); $\alpha$ is –1.0 for 125 to 139 msec of To; $\alpha$ is –1.5 for 110 to 124 msec of To; $\alpha$ is –2.0 for 95 to 109 msec of To; $\alpha$ is –3.0 for 94 msec or shorter.

The general equation (1) or the table TB1 shows that one can calculate the parameter $\alpha$ by measuring the pulse wave propagation time To at rest.

Figure 1:
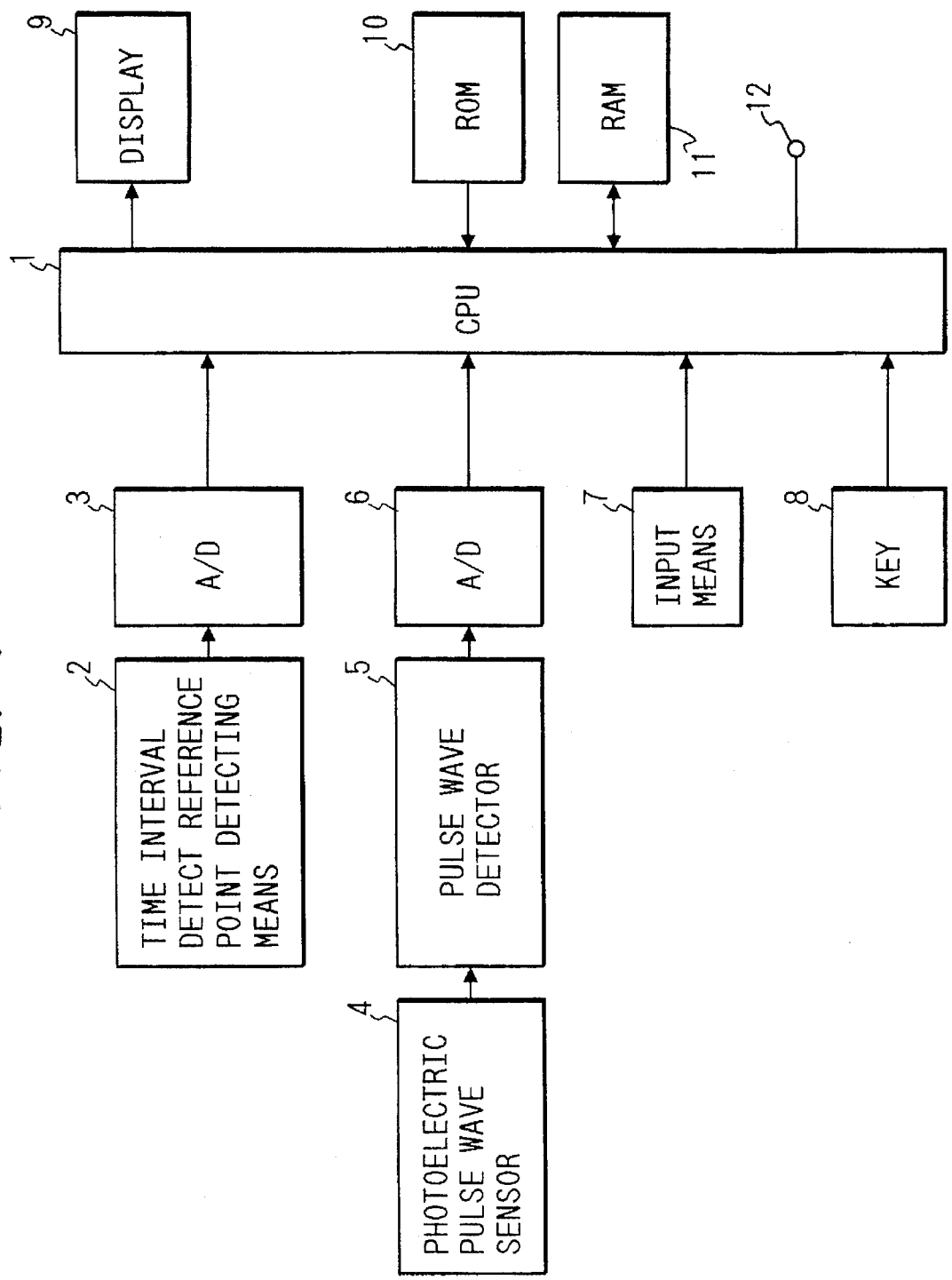
FIG. 1 is a block diagram showing a pulse-wave propagation time basis blood pressure monitor according to an embodiment of the present invention.

To be more specific, a program of the equation (1) or the table TB1 (FIG. 2) is stored in a memory (ROM) 10 in a system shown in FIG. 1. To obtain the parameter $\alpha$ corresponding to the measured pulse wave propagation time To, a CPU 1 reads the program of the equation (1) from the ROM 10 and executes the program or carries out the related process while referring to the contents of the table TB1.

After the parameter $\alpha$ is obtained, the parameter $\beta$ can be calculated by the following equation (2), using the blood pressure Po and the pulse wave propagation time To.

$$Po=\alpha To+\beta$$

$$\beta=Po-\alpha To \quad (2)$$

After the parameters $\alpha$ and $\beta$ are determined, the pulse wave propagation time T is successively measured, and then blood pressure P can successively be calculated by the following equation $$P=\alpha T+\beta \quad (3)$$

A pulse-wave propagation time basis blood pressure monitor according to the present invention is based on the above-mentioned technical idea.

FIG. 1 is a block diagram showing a pulse-wave propagation time basis blood pressure monitor according to the present invention.

The arrangement of the pulse-wave propagation time basis blood pressure monitor shown in FIG. 1 is used commonly for all of the blood pressure monitors as first to third embodiments of the present invention.

A time-interval detect reference point detecting portion 2 detects a time point where an aorta pulse pressure reaches the bottom of its amplitude variation, substantially simultaneously with generation of the electrocardiographic R wave. The output signal of the detecting portion 2 is converted into a digital signal by an A/D converter 3 and inputted to a CPU (central processing unit) 1. The time-interval detect reference point detecting portion 2 may be constructed with an electrode mounted on the chest of a subject and an electrocardiographic R wave detector connected to the electrode.

The time-interval detect reference point detecting portion 2 may include a photoelectric pulse wave sensor or a pulse pressure sensor for sensing a pulse wave in the aorta, and a pulse wave detector connected to the pulse pressure sensor.

A photoelectric pulse wave sensor 4 is attached to an ear lobe of a subject, for example, and senses a pulse wave in the peripheral blood vessel.

This sensor is not limited to the photoelectric pulse wave sensor but may be a pulse pressure sensor. The output signal of the photoelectric pulse wave sensor 4 is transmitted to a pulse wave detector 5 which detects a pulse wave at the location to which the sensor is attached. The output signal of the pulse wave detector 5 is converted into a digital signal by an A/D convertor 6 and input into the CPU 1.

A key 8 is used when the parameters $\alpha$ and $\beta$ proper to a subject are determined by the calibration.

An input member 7 is used for inputting a blood pressure value Po for calibration or, it is used for inputting the blood pressure value Po and a patient's height as patient information.

An instruction to output the measured data and an instruction to end the measurement are also entered from the input member 7.

The CPU 1 executes a process program in response to the signals from the A/D converters 3 and 6, the key 8, and the input member 7, and displays the results of executing the process program by a display 9, and output measured data to an external output connector 12.

The display 9 and the external output connector 12 form measuring data output device.

The process program is stored in a memory (ROM) 10 connected to the CPU 1.

The ROM 10 stores the general equation (1) for calculating the parameter $\alpha$ by using the pulse wave propagation time To, as mentioned above. Alternatively, the ROM 10 stores the table TB1 shown in FIG. 2, which is for obtaining the parameter $\alpha$ by using the pulse wave propagation time To.

Further, the ROM 10 stores the general equation (14) for obtaining the parameter $\alpha$ by using a pulse pressure Pa. In the arrangement of claim 4, the ROM 10 stores the table TB2 shown in FIG. 3.

Data being processed is stored in a RAM 11 connected to the CPU 1.

The CPU 1 forms the pulse-wave propagation time measuring section and the first to third computing device, forms the pulse-wave propagation time measuring section, the pulse pressure computing device, and the first to third computing device, or forms the pulse-wave propagation time measuring section, and the first to fifth computing device.

The operation of the pulse-wave propagation time basis blood pressure monitor thus constructed will be described with reference to a flowchart shown in FIG. 4.

In a step S1, it is checked whether or not the parameters $\alpha$ and $\beta$ proper to a subject are prepared. If these parameters are not prepared, the key 8 is operated.

In a step S2, a blood pressure of a subject is measured by using a blood pressure monitor with a cuff, and a blood pressure value Po for calibration is entered from the input member 7.

The blood pressure value Po entered is stored into the RAM 11.

In a step S3, the CPU 1 receives data from the A/D converters 3 and 6 and processes the data, and measures the pulse wave propagation time To for calibration immediately after the blood pressure value Po is measured. The measured pulse wave propagation time To is written into the RAM 11.

Subsequently, in a step S4, the parameter $\alpha$ is obtained using the pulse wave propagation time To measured for calibration while referring to the general equation (1) or the table TB1 shown in FIG. 1, which is stored in the ROM 10.

In a step S5, the blood pressure value Po for calibration read out of the RAM 11, the pulse wave propagation time To, and the parameter α are processed by the CPU 1, the parameter β is determined using the equation (2) and written into the RAM 11. In a step S6, the measurement of the blood pressure value P starts.

In the step S6, the data from the A/D converters 3 and 6 is processed by the CPU 1, the pulse wave propagation time T is measured, and the result is inputted to the RAM 11.

In a step S7, the CPU 1 executes the operation of the equation (3) by using the pulse wave propagation time T and the parameters α and β, thereby computing the blood pressure value P.

In a step S8, the measured blood pressure value P is written into the RAM 11, and is displayed by the display 9.

When the measuring data is not output and the measurement is not yet ended, the process from the steps S6 to S8 is repeated at preset periods, and the blood pressure measurement is successively carried out.

In a step S9, when an instruction to output the measuring data is entered from the input member 7, the measuring data stored in the RAM 11 is outputted through the external output connector 12 in a step S10.

In a step S11, when an instruction of the measurement end is entered from the input member 7, the process flow returns to the step S1.

In this case, when the blood pressure measurement is continued for the same subject, the blood pressure monitor needs only to carry out the process subsequent to the step S6 since the parameters α and β have been prepared.

Second Embodiment

The basic idea of a second embodiment of the present invention will be described.

At rest, the pulse pressure as the difference between the maximum blood pressure and the minimum blood pressure depends mainly on a volumetric elasticity of the blood vessel. Where the volumetric elasticity of the blood vessel is large, the pulse pressure is large, and where the volumetric elasticity of the blood vessel is large, the parameter α is large.

Where the volumetric elasticity of the blood vessel is small, the pulse pressure is small, and where the volumetric elasticity of the blood vessel is small, the parameter α is small.

Accordingly, there is a correlation between the pulse pressure and the parameter α.

The present invention is based on this knowledge.

The relationship between the pulse pressure at rest and the parameter α at rest was measured. The measurement was carried out on a total of 46 subjects including men of health and patients of 22 to 80 years old. The results of the measurement are as shown in FIG. 8.

Figure 8:
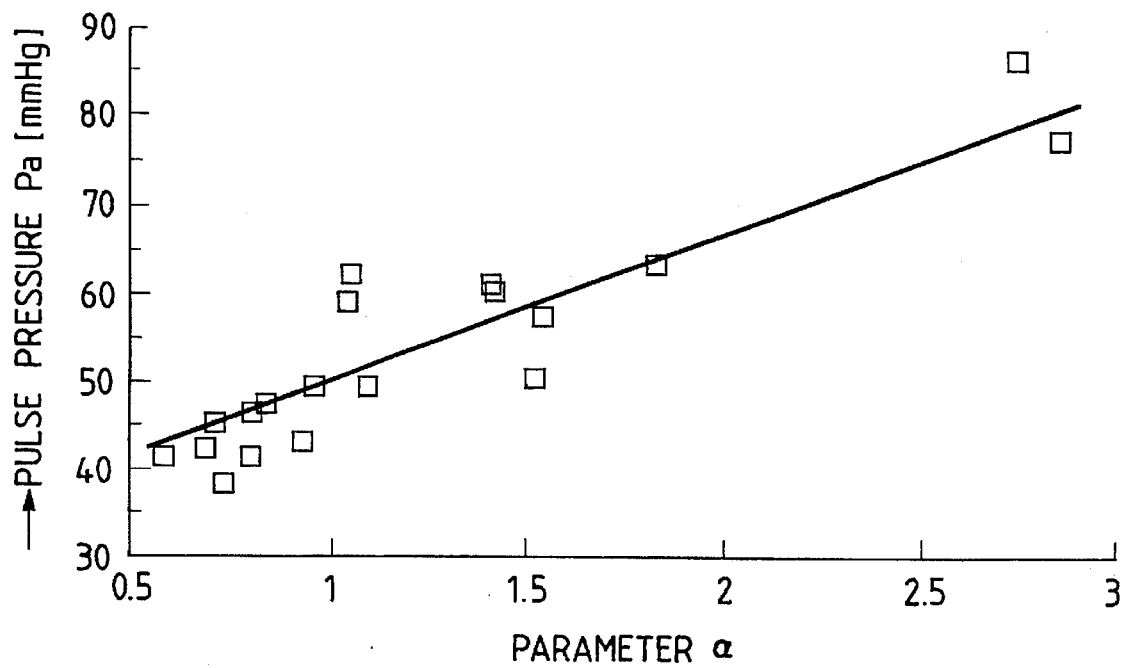
FIG. 8 is a graph showing the relationship between the pulse pressure and the parameter α, both being actually measured.

As seen from the graph of FIG. 8, the pulse pressure Pa and the parameter α can be expressed by the following equations $$pa = 16\alpha + 34$$

$$\alpha = (Pa - 34)/16 \qquad (4)$$

The relationship between the pulse pressure Pa and the parameter α may approximately be described by a table TB2 as shown in FIG. 3 on the basis of the equation (4). In the table TB2, the pulse pressure Pa is segmented every 10 mmHg.

As shown, in the table TB2, α (parameter) is −0.7 for 45 mmHg or lower of Pa (pulse pressure); α is −1.0 for 46 to 55 mmHg of Pa; α is −1.5 for 56 to 65 mmHg; α is −2.0 for 66 to 75 mmHg of Pa; α is −3.0 for 76 mmHg or higher of Pa.

The general equation (4) or the table TB2 shows that one can calculate the parameter α by measuring the pulse pressure Pa at rest.

To be more specific, a program of the equation (4) or the table TB2 (FIG. 3) is stored in the memory (ROM) 10. To obtain the parameter α corresponding to the pulse pressure Pa, the CPU 1 reads the program of the equation (4) from the ROM 10 and executes the program or carries out the related process while referring to the contents of the table TB2.

After the parameter α is obtained, the parameter β can be calculated by the equation (2), using the blood pressure Po and the pulse wave propagation time To measured for calibration.

After the parameters α and β are determined, the pulse wave propagation time T is successively measured, and then blood pressure P can successively be calculated by the equation (3). A pulse-wave propagation time basis blood pressure monitor according to the present invention is bared on the above-mentioned technical idea.

Figure 5:
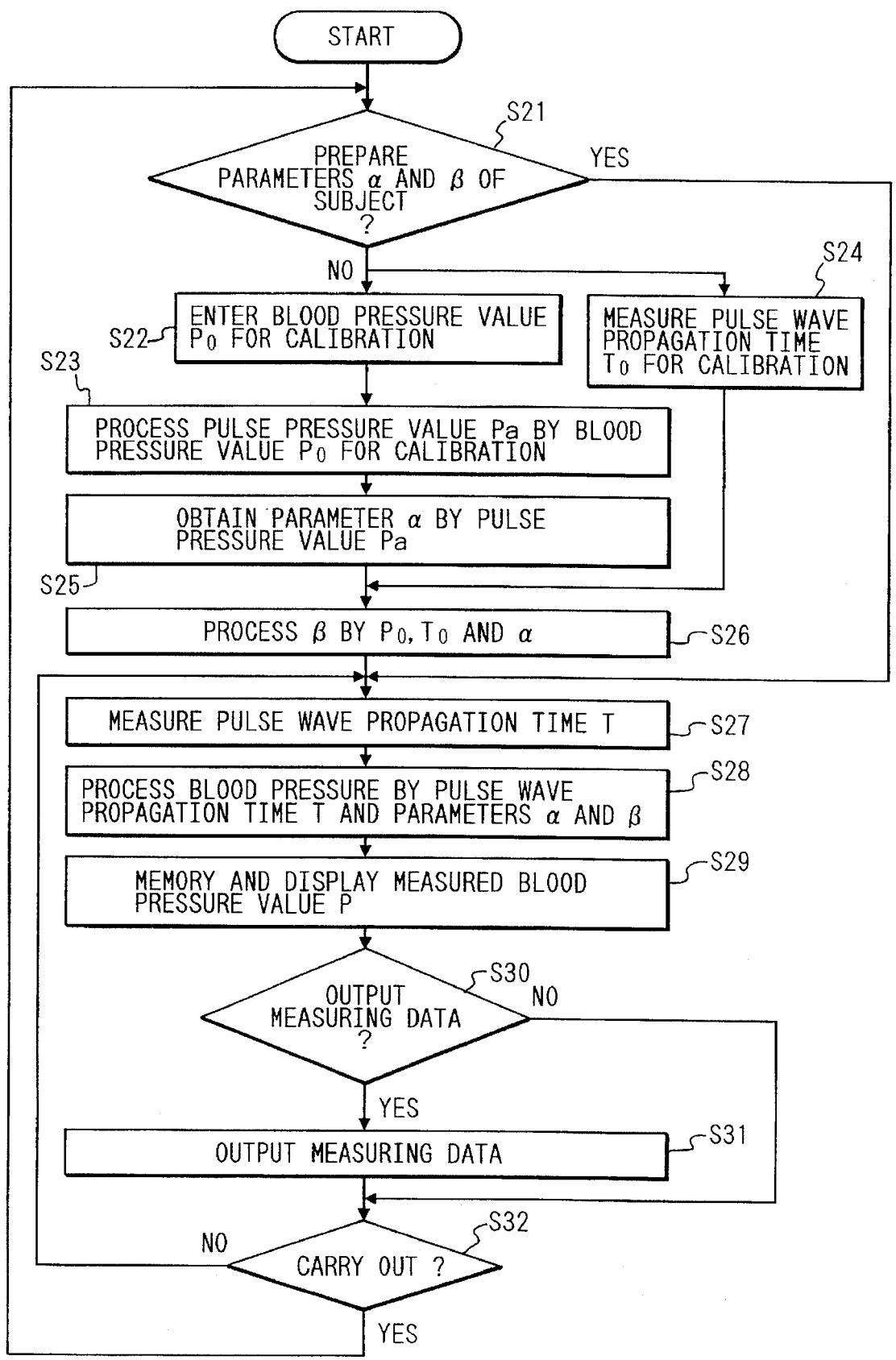
FIG. 5 is a flowchart showing the operation of a pulse-wave propagation time basis blood pressure monitor according to a second embodiment of the present invention.

The operation of second embodiment of the present invention will be described with reference to a flowchart of FIG. 5.

Figure 4:
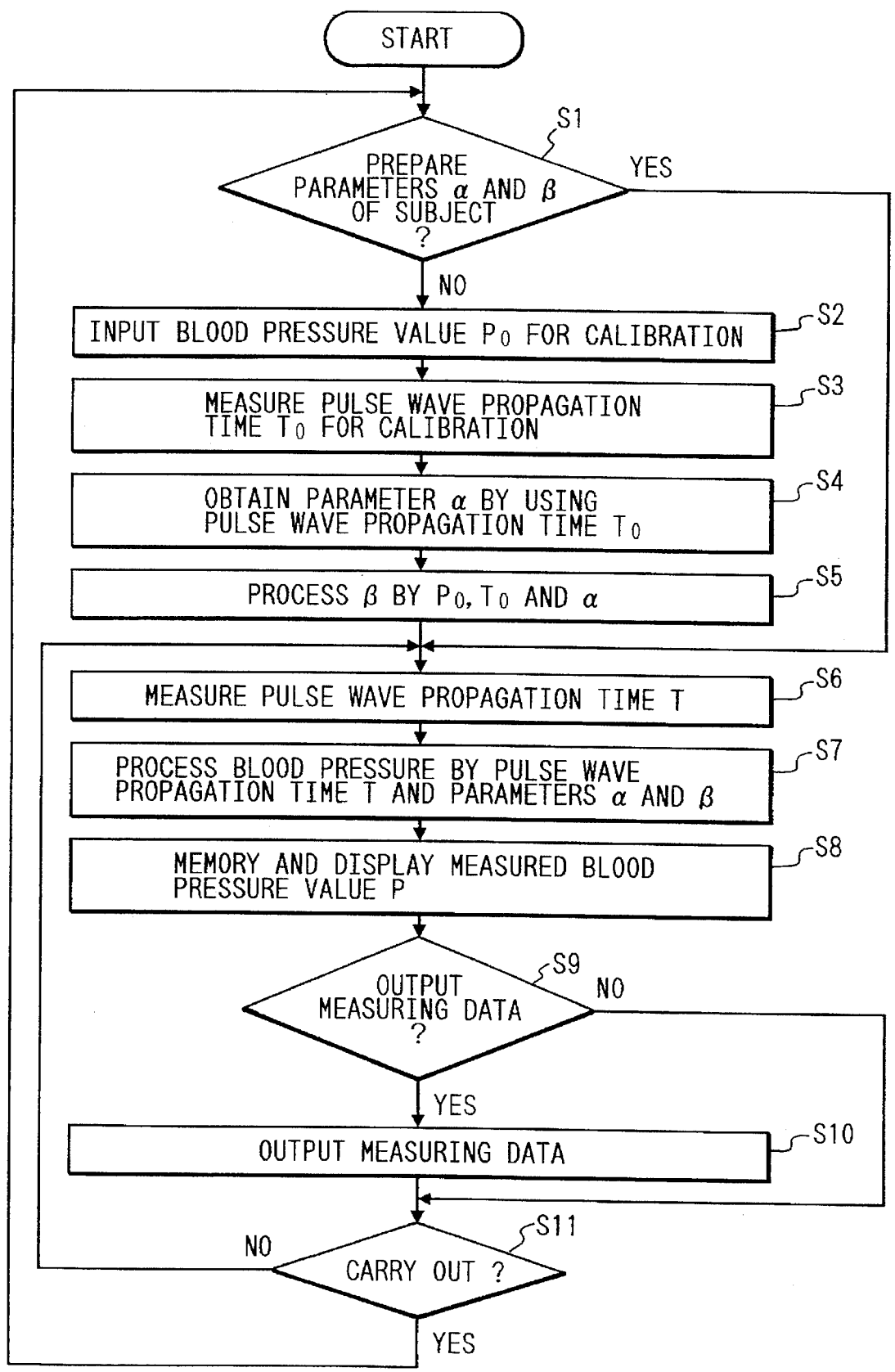
FIG. 4 is a flowchart showing the operation of a pulse-wave propagation time basis blood pressure monitor according to a first embodiment of the present invention.

In a step S21, as in the flowchart of FIG. 4, it is checked whether or not the parameters α and β proper to a subject are prepared. If these parameters are not prepared, the key 8 is operated.

In a step S22, a blood pressure of a subject is measured by using a blood pressure monitor with a cuff, and a blood pressure value Po for calibration is entered from the input member 7. The blood pressure value Po entered is stored into the RAM 11.

In a step S23, a pulse pressure value as the difference between a peak blood pressure and a bottom blood pressure is computed, as a pulse pressure value Pa for calibration, from the blood pressure value Po inputted for calibration.

The computed pulse pressure value Pa is written into the memory 11.

In a step S24, the CPU 1 processes the data from the A/D converters 3 and 6 in parallel with the process of the steps S21 and S22, whereby the pulse wave propagation time To for calibration is measured.

The measured pulse wave propagation time To is written into the RAM 11. The process of the step S24 may be carried put after the blood pressure measurement, as in the process of the FIG. 4 flowchart.

In a step S25, the parameter α is obtained using the pulse pressure value Pa measured for calibration while referring to the general equation (4) or the table TB2 shown in FIG. 3, which is stored in the ROM 10.

In a step S26, the blood pressure value Po for calibration read out of the RAM 11, the pulse wave propagation time To, and the parameter α are processed by the CPU 1, the parameter β is determined using the equation (2) and written into the RAM 11.

After the parameters α and β are determined, the process from the steps S27 to S32 is carried out. In the process, the pulse wave propagation time T is measured, the blood pressure value P is calculated, and if necessary, the measuring data is outputted.

The process from the steps S27 to S32 is similar to the process from the steps S6 to S11.

Third Embodiment

The basic idea of a third embodiment of the present invention will be described.

A method for obtaining the parameter α by using a change of a hydrostatic pressure between the heart and a pules wave measuring position at the time of postural change, and the pulse-wave propagation time difference, will be described.

In this case, it is presumed that the blood pressure is not varied at the time of postural change (from the supine position to the sitting position or the standing position).

When a subject changes his postural from the supine position to the sitting position or the standing position, a change ΔP of the hydrostatic pressure applied to the artery continuous to the ascending aorta, brachiocephalic artery, carotid artery, and a pulse wave sensor mounting position (generally the ear lobe) in the peripheral blood vessel, is expressed by $$\Delta P = \rho \cdot g \cdot h \quad (5)$$

where

ρ:specific gravity (1.055) of the blood
g:gravitational constant
h:difference between the height from the heat to the center (gravity center) of the artery continuous to the ascending aorta, brachiocephalic artery, carotid artery, and a pulse wave sensor mounting position (generally the ear lobe) in the peripheral blood vessel when the subject is at the sitting position and the height from the heat to the center (gravity center) of the artery continuous to the ascending aorta, brachiocephalic artery, carotid artery, and a pulse wave sensor mounting position (generally the ear lobe) in the peripheral blood vessel when the subject is at the supine position. The height difference h can be estimated from a subject's height H, and mathematically be expressed by $$h = a \cdot H \quad (6)$$

where a is constant, about 0.06.

ΔT representative of the difference between a pulse wave propagation time T1 measured at the supine position and a pulse wave propagation time T2 measured at the sitting position is expressed by $$\Delta T = T1 - T2 \quad (7)$$

The hydrostatic pressure change ΔP at the time of postural change and the pulse-wave propagation time difference ΔT define the parameter α as follows:

$$\alpha = \Delta P / \Delta T \quad (8)$$

After the parameter α is obtained, the parameter β can be calculated using the blood pressure Po and the pulse wave propagation time T1 or T2 measured for calibration.

After the parameters α and β are determined, the pulse wave propagation time is successively measured, and then blood pressure can successively be calculated. A pulse-wave propagation time basis blood pressure monitor according to the present invention is based on the above-mentioned technical idea.

Figure 6:
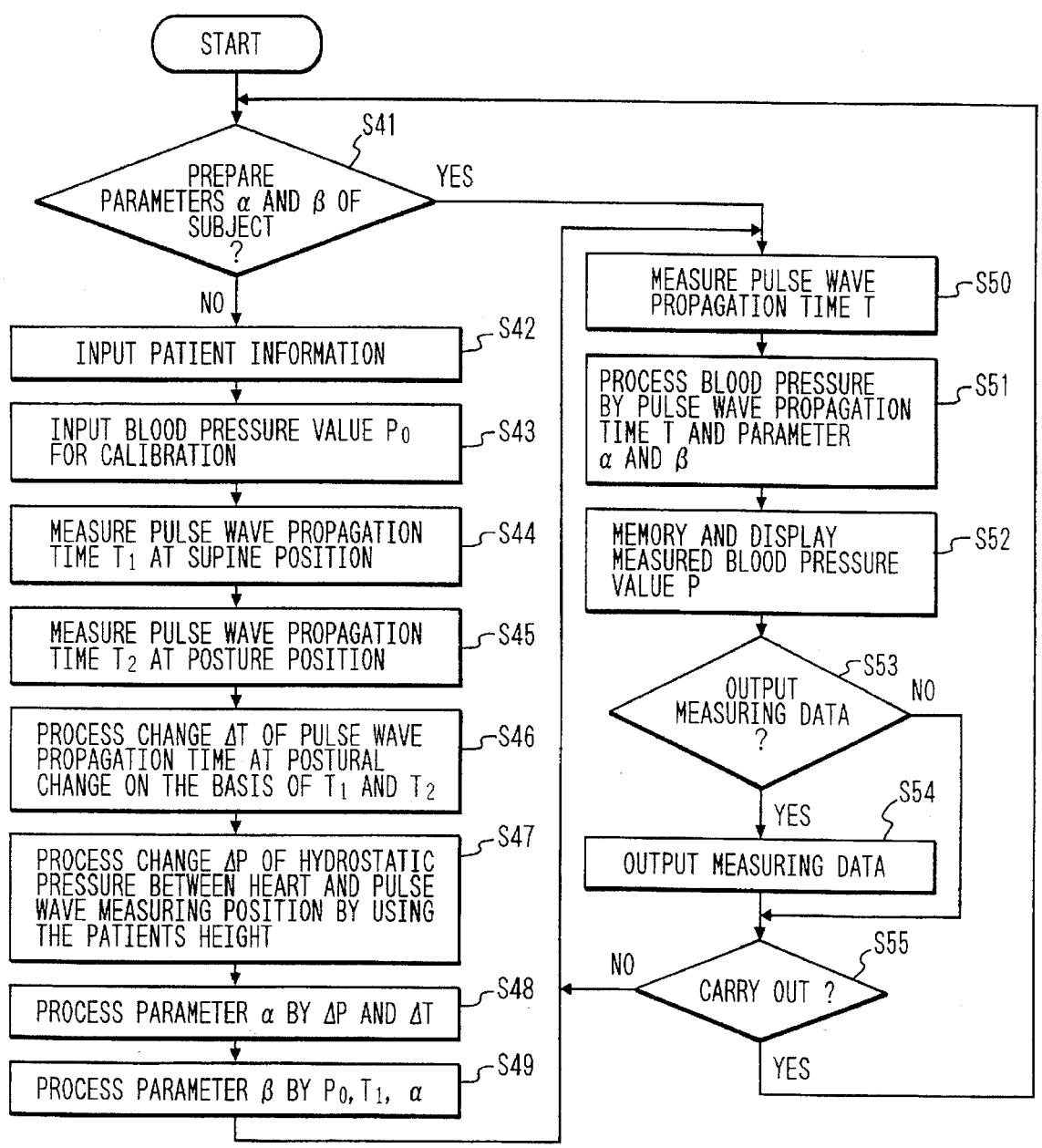
FIG. 6 is a flowchart showing the operation of a pulse-wave propagation time basis blood pressure monitor according to a third embodiment of the present invention.

The operation of third embodiment of the present invention will be described with reference to a flowchart of FIG. 6.

In a step S41, it is checked whether or not the parameters α and β proper to a subject are prepared. If these parameters are not prepared, the key 8 is operated.

In a step S42, a patient's height H as patient information is entered from the input member 7 and stored into the memory 11.

In a step S43, a blood pressure of a subject is measured by using a blood pressure monitor with a cuff, and a blood pressure value Po for calibration is entered from the input member 7.

The blood pressure value Po entered is stored into the RAM 11.

In a step S44, the subject is set at the supine position, the CPU 1 processes the data from the A/D converters 3 and 6. The pulse wave propagation time T1 for calibration immediately after the blood pressure value Po is measured is measured.

The measured pulse wave propagation time T1 is written into the RAM 11.

Subsequently, in a step S45, the posture of the subject is changed from the supine position to the sitting position, and the data from the A/D converters 3 and 6 is processed by the CPU 1, thereby to measure the pulse wave propagation time T2 for calibration. The measured pulse wave propagation time T2 is written into the RAM 11.

Alternatively, the subject's posture is changed to the standing position, and the pulse wave propagation time T2 may be measured. In a step S46, the CPU 1 carries out the equation (7) using the pulse wave propagation time T1 and T2, thereby computing a change ΔT of the pulse wave propagation time at the time of postural change.

In the subsequent step S47, the CPU 1 computes the equations (5) and (6) using the patient's height H, thereby obtaining a change ΔP of the hydrostatic pressure between the heat and a pulse wave measuring position at the time of postural change.

Alternatively, the subject's sitting height may be used for computing a change ΔP of the hydrostatic pressure.

To improve the accuracy, after the postural change, the blood pressure is measured again. If there is a change of the blood pressure, the hydrostatic pressure change is added to the computed hydrostatic pressure for the change.

In the next step S48, the CPU 1 computes the equation (8) by using a change ΔP of the hydrostatic pressure at the time of postural change and a change ΔT of the pulse wave propagation time, thereby to compute the parameter α.

In a step S49, the CPU 1 carries out the computing process using the blood pressure value Po inputted for calibration, the pulse wave propagation time T1, and the parameter α, thereby to determine the parameter β.

After the parameters α and β are determined, a blood pressure value P is computed by using the measured pulse wave propagation time T through the steps S50 to S55, and if necessary, the computed blood pressure is outputted. The process from the step S50 to the step S55 is like the process from the step S6 to the step S11 in FIG. 4.

As seen from the foregoing description, the blood pressure monitor of the present invention determines the parameter α by using the pulse wave propagation time measured for calibration, through the general equation or the table. If the parameter α is determined, the parameter β can be determined using the parameter α, the blood pressure value inputted for calibration, and the pulse wave propagation time.

Thus, the blood pressure measurement necessary for the calibration to determine the parameters α and β must be done only one time, not plural times. There is no need of doing the stress test which is accompanied by a great variation of the blood pressure.

As a result, the stress to the subject is lessened and the time for calibration is short.

Further, there is no need of a stress test device or a blood pressure monitor exclusively used for the stress test. This leads to reduction of the device cost.

According to the present invention, the parameter α can be determined using the pulse pressure calculated for calibration, through the table or the equation. Thereafter, the parameter β can be determined using the parameter α, the blood pressure value, and the pulse wave propagation time.

Also in this invention, the blood pressure measurement necessary for the calibration to determine the parameters α and β must be done only one time. The present invention has the useful effects comparable with those of the invention.

As blood pressure monitor of the present invention determines the parameter α by using the patient's height as patient information and the pulse wave propagation time difference measured at the time of postural change. The parameter β can be determined using the parameter α, the blood pressure value inputted for calibration, and the pulse wave propagation time.

Also in this invention, the blood pressure measurement necessary for the calibration to determine the parameters α and β may be only the blood pressure measurement at rest. The effects of this invention are also comparable with those of the invention.

Moreover, the parameters α processed by the methods of the present invention described above relate to the volumetirc elasticity of the vessel. Thus, when the parameter α is displayed on the display 9, it is possible to confirm the degree of arteriosclerosis of the subject at the same time of confirming the blood pressure.

What is claimed is:

1. A pulse-wave propagation time basis blood pressure monitor comprising:

a memory for storing information representing a relationship between pulse wave propagation times and values of a parameter α, each of said pulse wave propagation times being derived from data gathered from a number of subjects;

input means for inputting a blood pressure value of a subject, for calibration;

time-interval detect reference point detecting means for detecting a time of occurrence of a pulse wave in the aorta of a subject;

pulse wave detecting means for detecting a pulse wave which appears in a peripheral blood vessel after said pulse wave appears in the aorta;

pulse-wave propagation time measuring means for measuring pulse wave propagation time from signals output from said time-interval detect reference point detecting means and said pulse wave detecting means, wherein a first measured pulse wave propagation time is used for calibration;

first computing means for determining the parameter α which corresponds to said pulse wave propagation time used for calibration based upon the information stored in said memory;

second computing means for determining a parameter β by using said blood pressure value input for calibration, said pulse wave propagation time measured for calibration, and said parameter α determined by said first computing means;

third computing means for computing a blood pressure value in accordance with another pulse wave propagation time measured by said pulse-wave propagation time measuring means, and the parameters α and β; and measured data output means for outputting at least one of said blood pressure value and said parameter α.

2. The pulse-wave propagation time basis blood pressure monitor according to claim 1, wherein said information includes one of a predetermined equation and a table describing the relationship between said pulse wave propagation times and said values of said parameter α stored in said memory.

3. A pulse-wave propagation time basis blood pressure monitor comprising:

a memory for storing information representing a relationship between pulse pressure values and values of a parameter α, said pulse pressure values being derived from data gathered from a number of subjects;

input means for inputting a blood pressure value of a subject, for calibration;

pulse pressure computing means for computing a pulse pressure for calibration using said blood pressure value received from said input means;

time-interval detect reference point detecting means for detecting a time of occurrence of a pulse wave in the aorta of the subject;

pulse wave detecting means for detecting a pulse wave which appears in a peripheral blood vessel after said pulse wave appears in the aorta;

pulse-wave propagation time measuring means for measuring pulse wave propagation time from output signals of said time-interval detect reference point detecting means and said pulse wave detecting means, wherein a first measured pulse wave propagation time is used for calibration;

first computing means for determining the parameter α which corresponds to said pulse pressure for calibration computed for the subject based upon the information stored in said memory;

second computing means for determining a parameter β by using said blood pressure value input for calibration, said pulse wave propagation time used for calibration, and the parameter α determined by said first computing means;

third computing means for computing a blood pressure value by using another pulse wave propagation time measured by said pulse-wave propagation measuring means, and the parameters α and β; and measured data output means for outputting at least one of said blood pressure value and said parameter α.

4. The pulse-wave propagation time basis blood pressure monitor according to claim 3, wherein said information includes one of a predetermined equation and a table describing the relationship between said blood pressure values and said values of said parameter α stored in said memory.

5. A pulse-wave propagation time basis blood pressure monitor comprising:

first input means for inputting at least a patient's height value as patient information;

second input means for inputting a blood pressure value for calibration;

time-interval detect reference point detecting means for detecting a time of occurrence of a pulse wave in the aorta of the patient;

pulse wave detecting means for detecting a pulse wave which appears in a peripheral blood vessel after said pulse wave appears in the aorta;

pulse-wave propagation time measuring means for measuring pulse wave propagation time, at a supine position and at one of a sitting and standing position, from output signals of said time-interval detect reference point detecting means and said pulse wave detecting means, wherein a first measured pulse wave propagation time in one of said supine position, said sitting position and said standing position is used for calibration;

first computing means for computing a change ΔT of said pulse wave propagation time at a time of postural change by using a pulse wave propagation time for calibration measured at said supine position and a pulse wave propagation time for calibration measured at said one of a sitting position and a standing position;

second computing means for computing a change ΔP of a hydrostatic pressure between the heart and a pulse wave measuring position at the time of postural change, by using the patient's height as patient information;

third computing means for determining a parameter α by using said change ΔT of said pulse wave propagation time and said change ΔP of the hydrostatic pressure;

fourth computing means for determining a parameter β by using said blood pressure value input for calibration, said pulse wave propagation time used for calibration, and the parameter α determined by said third computing means;

fifth computing means for computing a blood pressure value by using another pulse wave propagation time measured by said pulse-wave propagation time measuring means, and the parameters α and β; and measured data output means for outputting at least one of said blood pressure value, said parameter α and said parameter β.

6. A method for measuring blood pressure using a pulse-wave propagation time basis blood pressure monitor comprising the steps of:

storing information describing the relationship between pulse wave propagation times and values of a parameter α in a memory, each of said pulse wave propagation times being derived from data gathered from a number of subjects;

inputting a blood pressure value of a subject for calibration;

detecting a reference point for detecting a time of occurrence of a pulse wave in the aorta of the subject;

detecting a pulse wave which appears in a peripheral blood vessel after said pulse wave appears in the aorta;

measuring a pulse wave propagation time from said reference point and said pulse wave which appears in the peripheral blood vessel for calibration;

determining the parameter α proper to the subject based upon the information stored in said memory corresponding to said pulse wave propagation time for calibration gathered from the subject;

determining a parameter β by using said blood pressure value input for calibration, said pulse wave propagation time for calibration, and the parameter α;

measuring a second propagation time of another pulse wave into the peripheral blood vessel;

computing a blood pressure value in accordance with said second pulse wave propagation time, and the parameters α and β; and outputting at least one of said blood pressure value, said parameter α and said parameter β.

7. A method for measuring blood pressure using a pulse-wave propagation time basis blood pressure monitor, comprising the steps of:

storing information describing the relationship between pulse pressure values and values of a parameter α in a memory, said pulse pressure values being derived from data gathered from a number of subjects;

inputting a blood pressure value of the subject for calibration;

computing a pulse pressure for calibration using said blood pressure value;

detecting a reference point for detecting a time of occurrence of a pulse wave in the aorta of the subject;

detecting a pulse wave which appears in a peripheral blood vessel after said pulse wave appears in the aorta;

measuring a pulse wave propagation time from said time of occurrence of said pulse wave in the aorta of the subject and said pulse wave of said peripheral blood vessel;

determining the parameter α proper to the subject based upon the information stored in said memory corresponding to said pulse pressure for calibration gathered from the subject;

determining a parameter β by using said blood pressure value input for calibration, said pulse wave propagation time and the parameter α;

measuring a second propagation time of another pulse wave into the peripheral blood vessel;

computing a blood pressure value by using said second pulse wave propagation time, and the parameters α and β; and outputting at least one of said blood pressure value, said parameter α and said parameter β.

* * * * *